(12) United States Patent
Kagan et al.

(10) Patent No.: US 6,693,207 B2
(45) Date of Patent: Feb. 17, 2004

(54) B-RING ESTRATRIENE DIOLS

(75) Inventors: Michael Z. Kagan, Plainsboro, NJ (US); Panolil Raveendranath, Monroe, NY (US); Syed M. Shah, East Hanover, NJ (US); Michael W. Winkley, Campbell Hall, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/164,149

(22) Filed: Jun. 5, 2002

(65) Prior Publication Data

US 2002/0156060 A1 Oct. 24, 2002

Related U.S. Application Data

(63) Continuation of application No. 09/063,451, filed on Apr. 21, 1998, now abandoned.
(60) Provisional application No. 60/046,847, filed on May 5, 1997.

(51) Int. Cl.[7] .............................. C07J 1/00; A61K 31/56
(52) U.S. Cl. ........................................ 552/642; 514/182
(58) Field of Search ........................... 514/182; 552/642

(56) References Cited

U.S. PATENT DOCUMENTS

| 2,834,712 A | 5/1958 | Beall et al. |
| 3,608,077 A | 9/1971 | Ginsig |
| 4,154,820 A | 5/1979 | Simoons |

FOREIGN PATENT DOCUMENTS

| DE | 635781 | 10/1936 |
| GB | 864231 | 3/1961 |

OTHER PUBLICATIONS

Physicians' Desk Reference, 48th edition, pp. 2594–2596, 1994.*
Renaud, Serge, Atherosclerosis, vol. 12(3), pp. 467–473, 1970.*
Pick et al., Progr. Biochem. Pharmacol., vol. 4, apges 354–362, 1968.*
Johnson, R. et al., J. Pharmac Sci., 67(9), Sep. 1978, pp. 1218–1224.
Starka, L. et al., J. Eur. Steroides, 1(1), 1966, pp. 37–45.
Bachman, W.E. et al., Helv. Chimica Acta., 42(6), Oct. 15, 1959, pp. 1790–1793.
Eimasry, A.H. et al., J. Pharmac. Sci., 59(4), Apr. 1970, pp. 449–458.
Kocovsky, P. et al., Collect. of Czech. Chemical Commun., 39(7), 1974, p. 1909.
Schuller, W.H. et al., J. Med. Chem., 14(5), May 1971, p. 466.
Peters, R.H. et al., J. Med. Chem., 32(7), Jul. 1989, pp. 1642–1652.
Physician Desk Reference, 48th Edition, pp. 2594–2596, 1994.
Goodman and Gilman, seventh edition, pp. 1420–1423, 1985.
Starka et al., J. Eur. Steroids, 1(1), pp. 37–45, 1966.
Banerjee et al., Indian J. Chem., vol. 7, pp. 529–532, 1969.

* cited by examiner

*Primary Examiner*—Barbara P. Badio
(74) *Attorney, Agent, or Firm*—Arnold S. Milowsky; Cozen O'Connor, Esq.

(57) ABSTRACT

This invention provides estrogenic agents having the formula

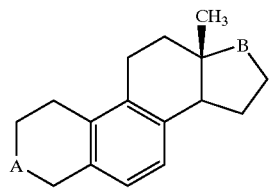

wherein
A and B are each, independently,

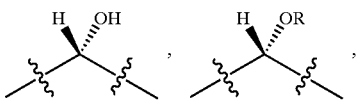

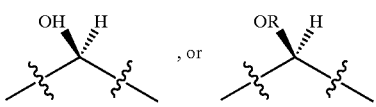

R is $SO_3^- X^+$;
$X^+$ is alkali metal, alkaline earth metal, ammonium, alkylammonium containing 1–6 carbon atoms, or dialkylammonium containing 1–6 carbon atoms in each alkyl group, or trialkylammonium containing 1–6 carbon atoms in each alkyl group;

with the proviso that at least one of A or B is

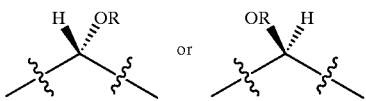

2 Claims, No Drawings

B-RING ESTRATRIENE DIOLS

This is a continuation of application Ser. No. 09/063,451, filed on Apr. 21, 1998, in which a CPA was filed on Oct. 4, 2000, now abandoned, which claims the benefit of Provisional Application No. 60/046,847 filed on May 5, 1997, the entire disclosure of which is hereby incorporated by reference.

BACKGROUND OF THE INVENTION

The use of naturally occurring estrogenic compositions of substantial purity and low toxicity such as PREMARIN (conjugated equine estrogens) has become a preferred medical treatment for alleviating the symptoms of menopausal syndrome, osteoporosis/osteopenia in estrogen deficient women and in other hormone related disorders. The estrogenic components of the naturally occurring estrogenic compositions have been generally identified as sulfate esters of estrone, equilin, equilenin, 17-β-estradiol, dihydroequilenin and 17-β-dihydroequilenin (U.S. Pat. No. 2,834,712). The estrogenic compositions are usually buffered or stabilized with alkali metal salts of organic or inorganic acids at a substantially neutral pH of about 6.5 to 7.5. Urea has also been used as a stabilizer (U.S. Pat. No. 3,608,077). The incorporation of antioxidants to stabilize synthetic conjugated estrogens and the failure of pH control with tris (hydroxymethyl)aminomethane (TRIS) to prevent hydrolysis is discussed in U.S. Pat. No. 4,154,820.

One of the compounds described herein, 5,7,9-estratriene-3β,17β-diol 3-sulfate ester sodium salt is a minor component of PREMARIN (conjugated equine estrogens).

DESCRIPTION OF THE INVENTION

In accordance with this invention, there are provided estrogenic agents having the formula

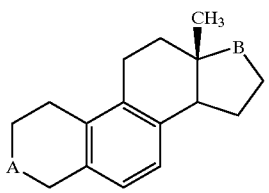

wherein
A and B are each, independently,

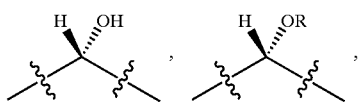

R is $SO_3^-X^+$;
$X^+$ is alkali metal, alkaline earth metal, ammonium, alkylammonium containing 1–6 carbon atoms, or dialkylammonium containing 1–6 carbon atoms in each alkyl group, or trialkylammonium containing 1–6 carbon atoms in each alkyl group;

with the proviso that at least one of A or B is

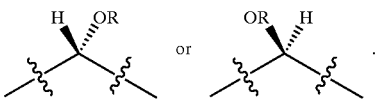

As 5,7,9-estratriene-3β,17β-diol 3-sulfate ester sodium salt is a minor component of PREMARIN (conjugated equine estrogens), this invention also provides 5,7,9-estratriene-3β,17β-diol 3-sulfate ester sodium salt in greater than one percent purity; and a compound consisting essentially of 5,7,9-estratriene-3β,17β-diol 3-sulfate ester sodium salt.

This invention further provides a composition of matter consisting essentially a compound having the formula

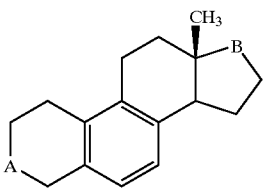

wherein
A and B are each, independently,

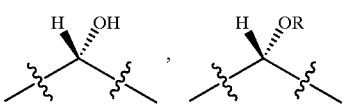

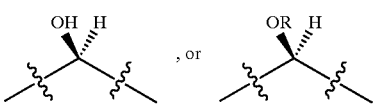

$X^+$ is alkali metal, alkaline earth metal, ammonium, alkylammonium containing 1–6 carbon atoms, or dialkylammonium containing 1–6 carbon atoms in each alkyl group, or trialkylammonium containing 1–6 carbon atoms in each alkyl group;
with the proviso that at least one of A or B is

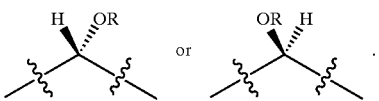

This invention additionally provides a method of providing estrogen therapy to a mammal in need thereof, which comprises administering an effective amount of a compound having the formula

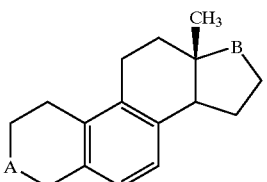

wherein
A and B are each, independently,

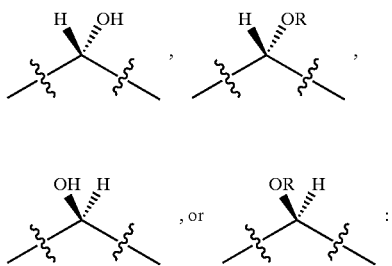

R is $SO_3^-X^+$;
$X^+$ is alkali metal, alkaline earth metal, ammonium, alkylammonium containing 1–6 carbon atoms, or dialkylammonium containing 1–6 carbon atoms in each alkyl group, or trialkylammonium containing 1–6 carbon atoms in each alkyl group;
to said mammal.

As used in accordance with this invention, treating covers treatment of an existing condition, ameliorating the condition, or providing palliation of the condition and inhibiting includes inhibiting or preventing the progress or development of the condition.

The compounds of this invention can be prepared from readily available starting materials. The following schemes show the preparation of representative compounds of this invention. For example, 5,7,9-estratriene-3β,17β-diol 3-sulfate ester sodium salt (7) can be prepared from 3β-hydroxy-5,7,9-estratriene-17-one according to Scheme I. 3β-Hydroxy-5,7,9-estratriene-17-one can be prepared according to D. Banerjee in Ind. Chim. Beige. Suppl. 2: 435 (1959).

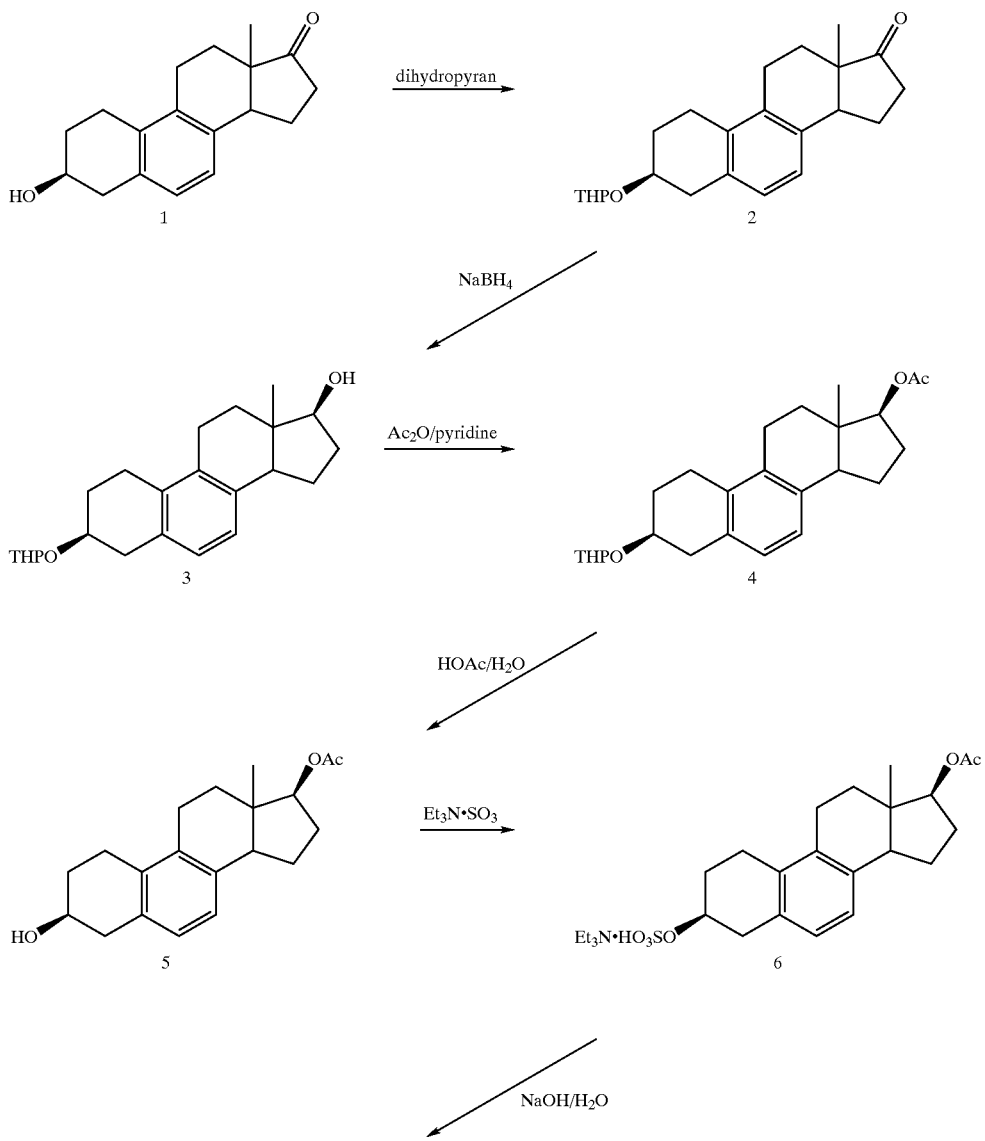

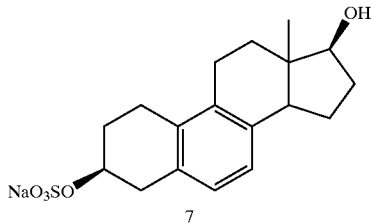

5,7,9-Estratriene-3β,17β-diol 3-sulfate ester sodium salt (7) can also be prepared by the selective sulfation of diol (8) as shown in Scheme II. Diol (8) can be prepared from (1) by the reduction of the 17-ketone with a reducing agent such as sodium borohydride.

Scheme II

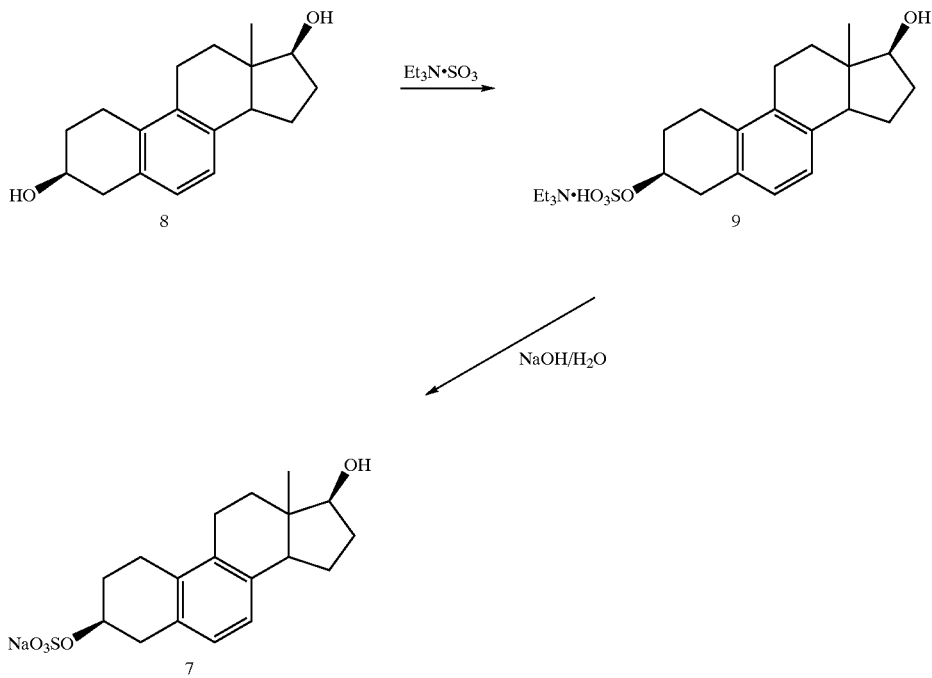

5,7,9-Estratriene-3β,17β-diol 3-sulfate ester sodium sat (7) can also be prepared according to Scheme III by the reduction of 3β-hydroxy-5,7,9-estratriene-17-one 3-sulfate ester sodium salt (10) with a reducing agent such as sodium borohydride.

Scheme III

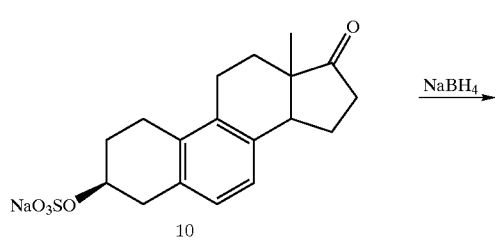

5,7,9-Estratriene-3α,17β-diol 3-sulfate ester sodium salt (17) can be prepared according to Scheme IV according to standard literature procedures. The introduction of the 3α-hdyroxyl group can be accomplished by the reduction of the 3-ketone (14) with a bulky reducing agent such as lithium tri-t-butoxy aluminumhydride.

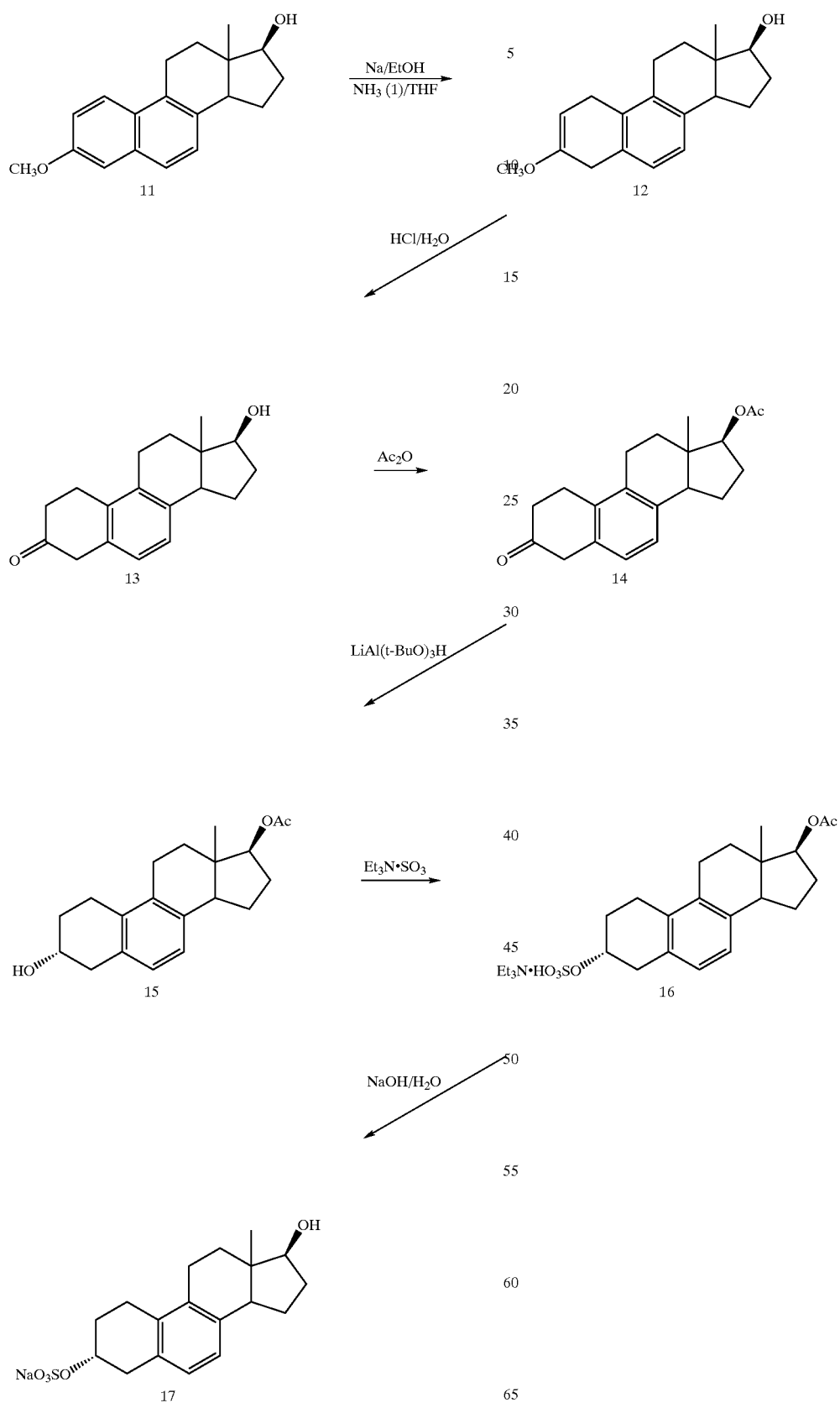

5,7,9-Estratriene-3α,17β-diol 3-sulfate ester sodium salt (17) can also be prepared according to Scheme V according to standard literature procedures.
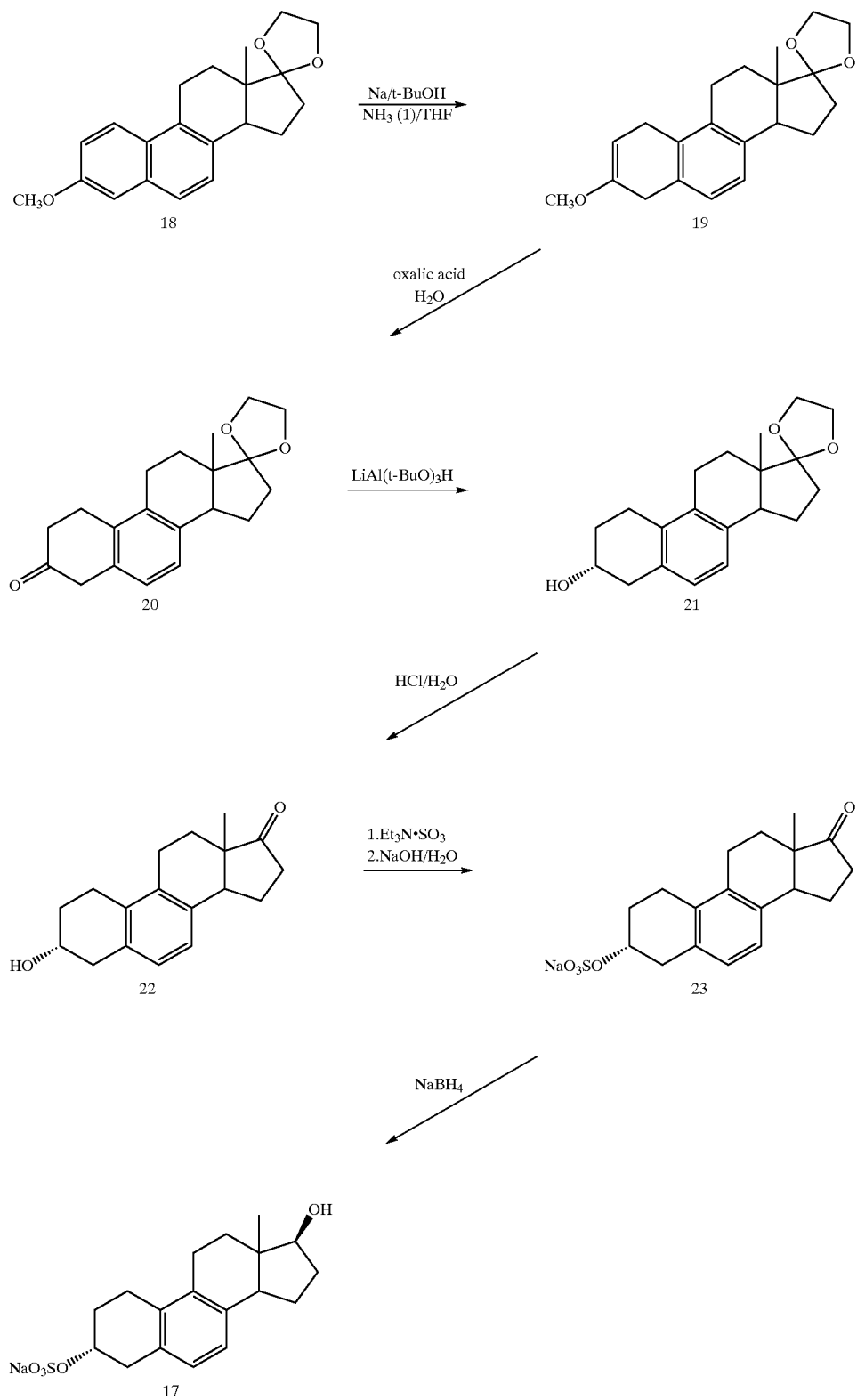

The preparation of 5,7,9-Estratriene-3β,17α-diol 3-sulfate ester sodium salt (32) can be prepared by standard methodology as shown in Scheme VI.
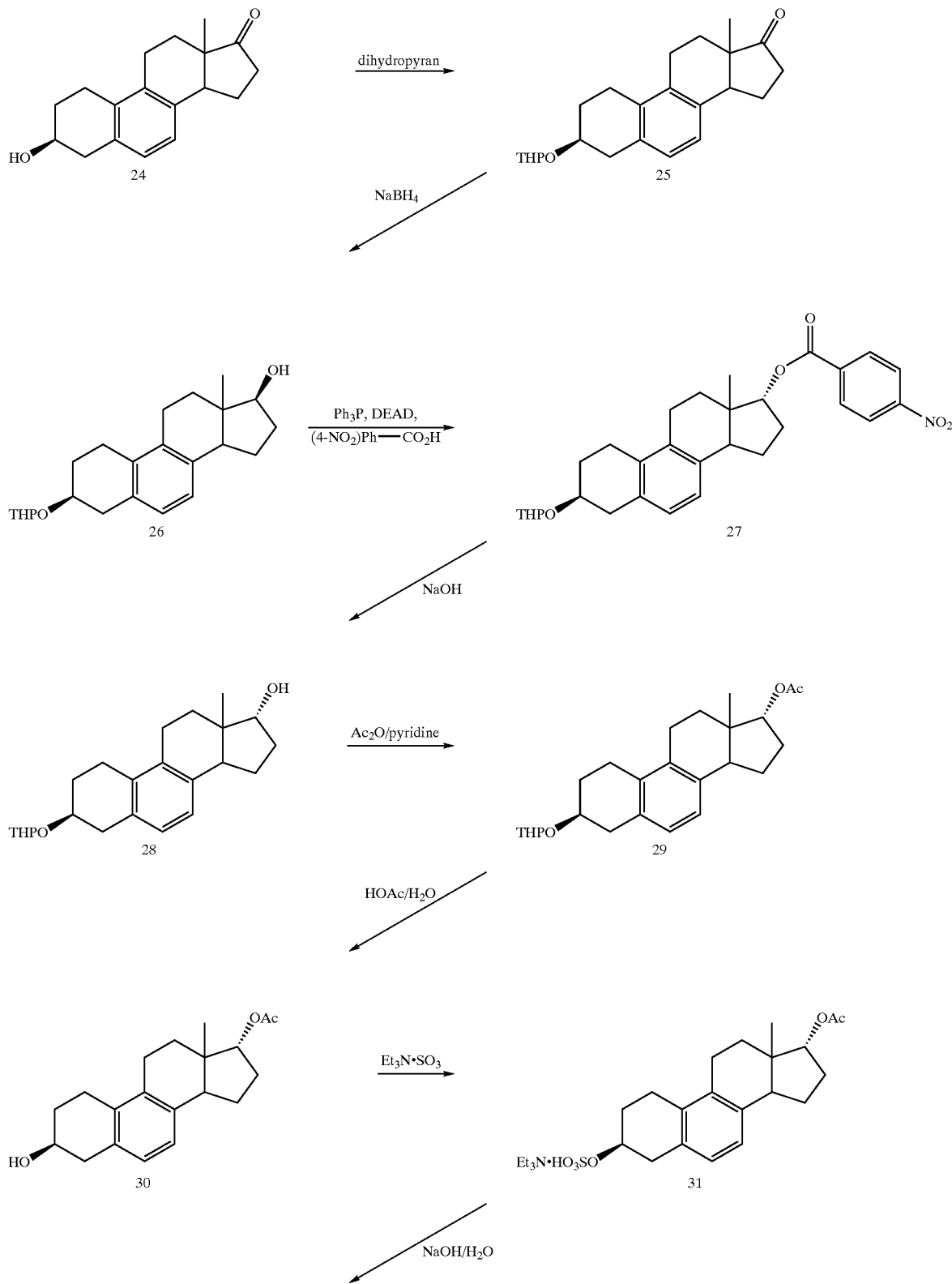
Scheme VI

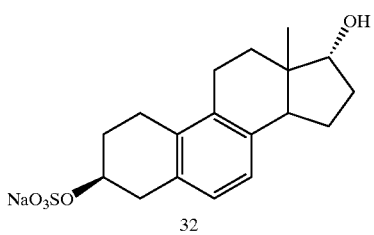

32

Compounds of this invention having the 3α,17α-configuration can be prepared by stereochemical inversion of the 3β-alcohol. For example, the 3β-hydroxyl group of compound (30) can be treated under the conditions used to effect the transformation from (26) to (27) to provide 3α,17α-stereochemistry. Sulfation hydroxyl groups at the 17-position for compounds of this invention can be accomplished via a protected 3-hydroxyl group or 3-ketone.

The compounds of this invention are estrogenic, as shown in the in vitro and in vivo standard pharmacological test procedures described below in which 5,7,9-estratriene-3β,17β-diol was evaluated as a representative compound of this invention.

Estrogen Receptor Binding

An initial evaluation examined the competitive binding properties of 5,7,9-estratriene-3β,17β-diol to the human estrogen receptor (hER-α) prepared as a soluble cell extract (cytosol). In this standard pharmacological test procedure, 5,7,9-estratriene-3β,17β-diol demonstrated no specific binding activity. However, when estrogen receptor binding was analyzed using a whole cell test procedure, specific binding was clearly demonstrated. This test procedure indicated an $IC_{50}$ of $2.3 \times 10^{-8}$ M for 5,7,9-estratriene-3β,17β-diol. This would be compared with a $K_i$ for estrone, equilin and equilinen of 51, 67 and 375 nM, respectively.

In Vitro Cotransfection Test Procedure

In this standard pharmacological test procedure, hER-α over-expressed in Chinese hamster ovary (CHO) cells infected with adeno-2x-ERE-tk-luciferase, an estrogen responsive reporter gene construct, cells were exposed to varying concentrations ($10^{-12}$–$10^{-5}$M) of 5,7,9-estratriene-3β,17β-diol for 24 hours. Cells were also exposed to 17β-estradiol at $10^{-9}$ M. Following the 24-hour treatment, cells were lysed and cell extracts assayed for luciferase activity. The results provided that 5,7,9-estratriene-3β,17β-diol had an $EC_{50}$ of approximately 30 nM. Using a similar test procedure, previous data indicate a 5.6 nM $EC_{50}$ for estrone.

In Vivo Uterotropic Activity

Immature rats were treated with doses of 0.2 and 2 mg/kg 5,7,9-estratriene-3β,17β-diol for three days (S.C.) as well as additional groups (n=6) of rats treated with 0.5 μg ethinyl estradiol and vehicle as positive and negative controls, respectively. Rats treated with 5,7,9-estratriene-3β,17β-diol had uterine weight gains at both concentrations demonstrating that 3β-hydroxy-5,7,9-estratriene-17-one was estrogenic.

The results of these standard pharmacological test procedures demonstrate that the compounds of this invention are estrogenic.

Based on the results obtained in the standard pharmacological test procedures, the compounds of this invention are useful in providing estrogen replacement therapy following ovariectomy or menopause, and in relieving symptoms related to estrogen deficiency, including vasomotor symptoms, such as hot flushes, and other menopausal related conditions, such as vaginal atrophy, vaginitis, and atrophic changes of the lower urinary tract which may cause increased urinary frequency, incontinence, and dysuria. The compounds of this invention are useful in preventing bone loss and in the inhibition or treatment of osteoporosis. The compounds of this invention are cardioprotective and they are useful in the treatment of atherosclerosis, ischemic disease, and hypertension. These cardiovascular protective properties are of great importance when treating postmenopausal patients with estrogens to prevent osteoporosis and in the male when estrogen therapy is indicated. Additionally, the compounds of this invention are useful in the suppression of lactation, and in the prophylaxis and treatment of mumps orchitis.

The compounds of this invention can be used alone as a sole therapeutic agent or can be used in combination with other agents, such as other estrogens, progestins, or and androgens.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.02 µg/kg–750 µg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

What is claimed is:

1. A compound having the formula

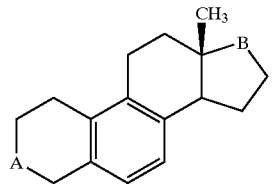

wherein
A and B are each, independently,

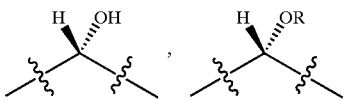

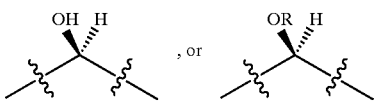

R is $SO_3^-X^+$;

$X^+$ is alkali metal, alkaline earth metal, ammonium, alkylammonium containing 1–6 carbon atoms, or dialkylammonium containing 1–6 carbon atoms in each alkyl group, or trialkylammonium containing 1–6 carbon atoms in each alkyl group;

with the proviso that at least one of A or B is

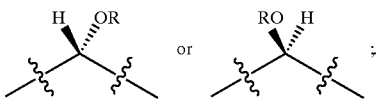

and further provided that when A is

2. 5,7,9-Estratriene-3β,17β-diol sulfate ester sodium salt in greater than one percent purity.

* * * * *